Oct. 14, 1958 F. MEILLAND Plant Pat. 1,760
ROSE PLANT
Filed Feb. 26, 1958
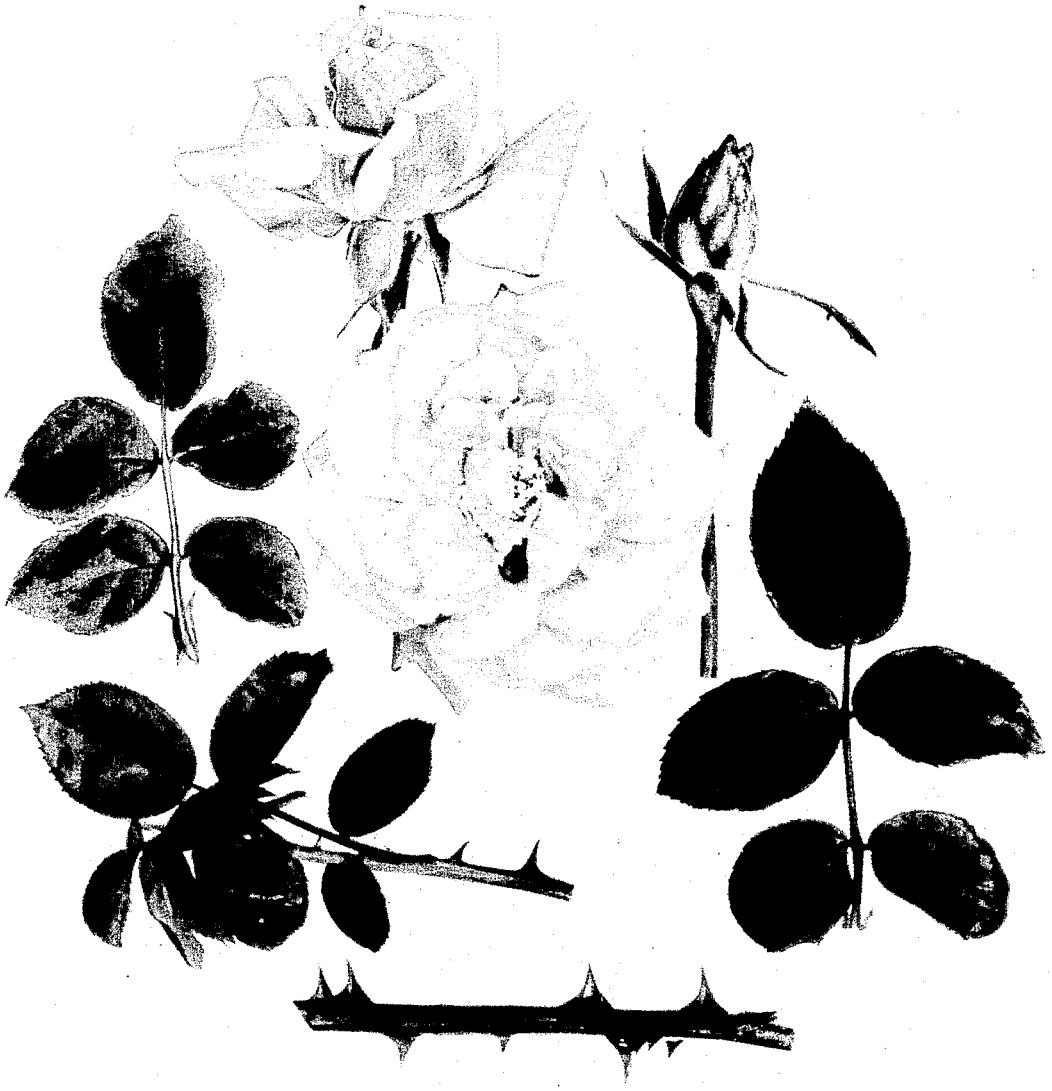
Inventor.
Francis Meilland
By: Robb & Robb
Attorneys.

United States Patent Office

Plant Pat. 1,760
Patented Oct. 14, 1958

1,760

ROSE PLANT

Francis Meilland, Cap d'Antibes, Alpes Maritimes, France, assignor to The Conard-Pyle Company, West Grove, Pa., a corporation of Pennsylvania Application February 26, 1958, Serial No. 717,798

1 Claim. (Cl. 47—61)

The present invention relates to a new and distinct variety of rose plant of the hybrid tea class, which was originated by me by crossing an unnamed and unpatented seedling derived from "Peace" (U. S. Plant Patent No. 591) × "Floradora" (unpatented) with the variety "Grand'mere Jenny" (U. S. Plant Patent No. 1,148).

The primary objective of this breeding was to produce a new rose variety which combines the most desirable characteristics of its parents. This objective was fully achieved, along with other improvements, as evidenced by the following unique combination of characteristics in the new variety which distinguish it from its parents, as well as from all other varieties of which I am aware:

(1) Excellent vigor and habit of the plant;
(2) Good floriferousness;
(3) Excellent form of the blooms; and
(4) A distinctive Iridescent Vermilion general color tonality of the opening blooms, which changes to Delft Rose color in the mature blooms.

Asexual reproduction of my new variety by budding, as performed in France and at West Grove, Pennsylvania, U. S. A., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Horticultural Color Chart of the British Color Council, except where general color terms of ordinary dictionary significance are obvious:

Type: Hardy; bush; outdoor; seedling; for cut flowers and for garden decoration.
Class: Hybrid tea.
Breeding: Seedling.—
*Seed parent.*—An unnamed and unpatented seedling derived from a cross of "Peace" × "Floradora."
*Pollen parent.*—"Grand'mere Jenny."
Propagation: Holds its distinguishing characteristics through succeeding propagations by budding.

*Flower*

Locality where grown and observed: West Grove, Pennsylvania, U. S. A.
Flowers borne: Singly to stem; on stems of medium length and normal strength.
Quantity of bloom: Abundant, outdoors.
Continuity: Continuous.
Fragrance: Slight. Nature—tea.
Bud:
*Peduncle.*—Medium long; heavy; stiff; rough; with medium number of brown hairs. Color—reddish.
*Before calyx breaks.*—Size—medium. Form—ovoid; with a conspicuous neck; with foliaceous appendages on the surface of the bud; with medium thick, little-cut foliaceous parts extending beyond the tip of the bud equal to ¼ or more of its length.
*As calyx breaks.*—Color—Maroon, Plate 1030, appearing black where first exposed to light.
*As first petal opens.*—Size—medium. Form—ovoid. Colors: outside— Chrysanthemum Crimson, Plate 824, blotched with Maroon, Plate 1030, and washed with Spirea Red, Plate 025 towards base, with point of attachment Dresden Yellow, Plate 64/1; inside—Geranium Lake, Plate 20/1, veined with Orient Red, Plate 819/1, with area surrounding base Signal Red, Plate 719, and with point of attachment Canary Yellow, Plate 2.
*Opening.*—Opens up well.
Bloom:
*Size (when fully open).*—Medium large; from 4 inches to 4½ inches.
*Petalage.*—Double; from 35 to 40 petals; arranged irregularly.
*Form.*—High-centered at first, but becoming open high-centered; petals being at first loosely rolled outward, but becoming tightly rolled outward later at maturity.
Petals: Thick; leathery; with inside velvety and outside satiny.
*Shape.*—Outer—ovate; with one notch. Intermediate—ovate; with one tooth. Inner—ovate; undulate; with one or two notches.

This description of a newly opened flower was made from a rose grown outdoors in the month of August, at West Grove, Pennsylvania, U. S. A.:

*Color.*—Outer petal: outside surface—Rose Opal, Plate 022, with lower margin of petal Cardinal Red, Plate 822, and with point of attachment Canary Yellow, Plate 2/2; inside surface—Delft Rose, Plate 020 at margin, shading into Claret Rose, Plate 021 and grading to Dutch Vermilion, Plate 717/1, with point of attachment Mimosa Yellow, Plate 602. Intermediate petal: outside surface—Cardinal Red, Plate 822/1; inside surface—Scarlet, Plate 19, sometimes with a narrow margin of Porcelain Rose, Plate 620 at outer edge, with point of attachment Canary Yellow, Plate 2. Inner petal: outside surface—unevenly distributed Claret Rose, Plate 021, with point of attachment Canary Yellow, Plate 2, surrounded by Canary Yellow, Plate 2/2; inside surface—Iridescent Vermilion, Plate 18, with margin of petal Dutch Vermilion, Plate 717/1, and with point of attachment Canary Yellow, Plate 2.

This description was made from a rose that was open for 3 days outdoors in the month of August, at West Grove, Pennsylvania, U. S. A.:

*Color.*—Outer petal: outside surface—Spinel Red, Plate 0023/1, with point of attachment Canary Yellow, Plate 2/3; inside surface—Delft Rose, Plate 020/1, with point of attachment Canary Yellow, Plate 2/3. Inner petal: outside surface—Spinel Red, Plate 0023, shading to Canary Yellow, Plate 2/1 at base; inside surface—Iridescent Delft Rose, Plate 020/1, with point of attachment Canary Yellow, Plate 2/1.
*General color effect.*—Newly opened flower—from Iridescent Vermilion, Plate 18/1 to Dutch Vermilion, Plate 717/3. 3-days open—Delft Rose, Plate 020/1.
*Behavior.*—Drop off cleanly.
*Flower longevity.*—On bush in garden—4 days in August. Cut roses grown outdoors and kept at living-room temperature—3 days in August.

*Reproductive Organs*

Stamens: Many; arranged regularly about pistils.
Filaments: Many; most with anthers; long. Color—Jasper Red, Plate 018, with basal quarter Yellow Ochre, Plate 07.
Anthers: All open at once; medium size; seldom an anther fused with a petaloid. Color—Lemon Yellow, Plate 4/2.
Pollen: Moderate. Color—gold.
Pistils: Few
Styles: Uneven; medium length; medium caliper; bunched.
Stigma: Color—yellow.
Ovaries: All enclosed in receptacle.
Hips: None.
Sepals: Permanent; moderately long; straight.
Seeds: None.

*Plant*

Foliage:

*Leaves.*—Compound of 5 leaflets; from normal abundance to abundant; medium size; heavy; leathery.

*Leaflets.*—Shape—ovoid, with apex acute. Base—obtuse. Margin—simply serrate.

*Color.*—Mature: upper surface—Parsley Green, Plate 00962; under surface—Sage Green, Plate 000861. Young: upper surface—Lettuce Green, Plate 861/1, overlaid with Maroon, Plate 1030; under surface—Erythrite Red, Plate 0027/1.

*Rachis (the supporting stem of the compound leaf).*—Medium caliper. Upper side—grooved; hairy. Under side—sparsely prickly.

*Stipules.*—Medium length; moderately narrow; with points of medium length turning out at an angle of more than 45°.

*Disease resistance.*—Comparable to that of the average variety grown under the same cultural conditions at West Grove, Pennsylvania, U. S. A.

Growth:

*Habit.*—Bushy; upright; much-branched.

*Growth.*—Free.

*Canes.*—Medium caliper.

*Main stems.*—Color—Fern Green, Plate 0862. Prickles—several; color—slightly lighter than Oxblood Red, Plate 00823/3. Hairs—none.

*Branches.*—Color—Fern Green, Plate 0862. Prickles—several; color—slightly lighter than Oxblood Red, Plate 00823/3. Hairs—none.

*New shoots.*—Color—Lettuce Green, Plate 861/1, except where exposed to the sun where overlying color of Oxblood Red, Plate 00823/3 predominates. Prickles—several; color—Oxblood Red Plate 00823/3. Hairs—few; color—Oxblood Red, Plate 00823/3.

I claim:

A new and distinct variety of rose plant of the hybrid tea class, substantially as herein shown and described, characterized particularly as to novelty by the unique combination of excellent vigor and habit of the plant, good floriferousness, excellent form of the opening blooms, and a distinctive Iridescent Vermilion general color tonality of the opening blooms which changes to Delft Rose color in the mature blooms.

No references cited.